(12) United States Patent
Nelson

(10) Patent No.: US 6,562,042 B2
(45) Date of Patent: May 13, 2003

(54) ORTHOPEDIC IMPLANT USED TO REPAIR INTERTROCHANTERIC FRACTURES AND A METHOD FOR INSERTING THE SAME

(76) Inventor: Owen A. Nelson, 164 Regency Dr., Uniontown, PA (US) 15401

( * ) Notice: Subject to any disclaimer, the term of this patent is extended or adjusted under 35 U.S.C. 154(b) by 113 days.

(21) Appl. No.: 09/775,266

(22) Filed: Feb. 1, 2001

(65) Prior Publication Data

US 2001/0034523 A1 Oct. 25, 2001

Related U.S. Application Data

(60) Provisional application No. 60/179,641, filed on Feb. 2, 2000.

(51) Int. Cl.$^7$ .......................... A61B 17/56; A61B 17/58; A61F 2/30
(52) U.S. Cl. .............................. 606/62; 606/65; 606/66; 606/72
(58) Field of Search .............................. 606/62, 63, 64, 606/65, 66, 72

(56) References Cited

U.S. PATENT DOCUMENTS 4,503,847 A 3/1985 Mouradian
4,697,585 A 10/1987 Williams (List continued on next page.)

FOREIGN PATENT DOCUMENTS

EP 0 251 583 A2 1/1988

OTHER PUBLICATIONS

Russell, Thomas A. et al., Richards Russell–Taylor Reconstruction Nail brochure, 1 page.

(List continued on next page.)

*Primary Examiner*—Henry Bennett
*Assistant Examiner*—Kathryn Ferko
(74) *Attorney, Agent, or Firm*—DKW Law Group, PC; Terry L. Schnell

(57) ABSTRACT

The present invention relates to a medical device used to repair intertrochanteric fractures of the femur and a method for inserting and using the same which includes in cooperation a hip screw, a gliding mechanism, an intramedullary nail, and a compression screw. The hip screw includes along a longitudinal axis an externally threaded portion as a bone screw for threadable insertion into the head of the femur and a hollow barrel portion, the barrel portion having a pair of opposed slots provided therein along the longitudinal axis of the hip screw. The hollow barrel portion optionally further includes internal or female threads within the barrel portion near the end of the hip screw opposite the bone screw for threadably engaging a compression screw. The gliding mechanism is retained within the barrel portion of the hip screw with a slidable fit and provides for lateral movement of the intramedullary nail along the longitudinal axis of the hip screw. The hip screw and the intramedullary nail are retained by the gliding mechanism at either a fixed angle of the intramedullary nail relative to the hip screw or a variable angle. The intramedullary nail is affixed to the gliding mechanism, as for example with a set screw or locking screw, to prevent relative motion between the gliding mechanism and the intramedullary nail. Upon securing the gliding mechanism to the intramedullary nail, in turn the hip screw and the intramedullary nail are affixed to one another, but due to the slidable fit of the gliding mechanism within the barrel of the hip screw and due to the slots in the hip screw, movement of the gliding mechanism/intramedullary nail assembly along the longitudinal axis of the hip screw can occur as the gliding mechanism glides within the barrel portion of the hip screw.

39 Claims, 11 Drawing Sheets

U.S. PATENT DOCUMENTS

| | | | |
|---|---|---|---|
| 4,776,330 A | | 10/1988 | Chapman et al. |
| 4,827,917 A | | 5/1989 | Brumfield |
| 4,946,459 A | | 8/1990 | Bradshaw et al. |
| 5,041,114 A | | 8/1991 | Chapman et al. |
| 5,176,681 A | | 1/1993 | Lawes et al. |
| 5,312,406 A | | 5/1994 | Brumfield |
| 5,356,410 A | | 10/1994 | Pennig |
| 5,454,813 A | | 10/1995 | Lawes |
| 5,531,748 A | | 7/1996 | de la Caffiniere |
| 5,562,666 A | | 10/1996 | Brumfield |
| 5,562,667 A | * | 10/1996 | Shuler et al. ............... 606/64 |
| 5,713,902 A | | 2/1998 | Friedl |
| 5,908,422 A | * | 6/1999 | Bresina ..................... 606/67 |
| 5,928,235 A | * | 7/1999 | Friedl ........................ 606/64 |
| 6,221,074 B1 | * | 4/2001 | Cole et al. .................. 606/62 |
| 6,228,086 B1 | * | 5/2001 | Wahl et al. ................. 606/67 |
| 6,235,031 B1 | * | 5/2001 | Hodgeman et al. .......... 606/64 |
| 6,443,954 B1 | * | 9/2002 | Bramlet et al. .............. 606/62 |
| 2002/0151898 A1 | * | 10/2002 | Sohngen et al. ............. 606/62 |

OTHER PUBLICATIONS

Zickel Nail brochure, 1 page.

Gamma Locking Nail brochure, 2 pages.

Richards IMHS system brochure, 2 pages.

Synthes Corp. Proximal Femoral Nail brochure, 2 pages.

Web pages for Howmedica for the Alta IM Rodding System and Grosse & Kempf Locking Nail System, 1997, 3 pages.

Smith & Nephew, "Compression Hip Screw Plates and Nails, Surgical Technique", 2000, pp. 1–77.

Taglang, Dr. G. et al., "Trochanteric Gamma Locking Nail" Operating Guide, pp. 1–32.

International Search Report for Application No. PCT/US01/03297, Feb. 2, 2000, 2 pages.

Web page printout of "BCM Dynamic Synthesis System", Lima–Lto spa, Udine, Italy, 1 page.

* cited by examiner

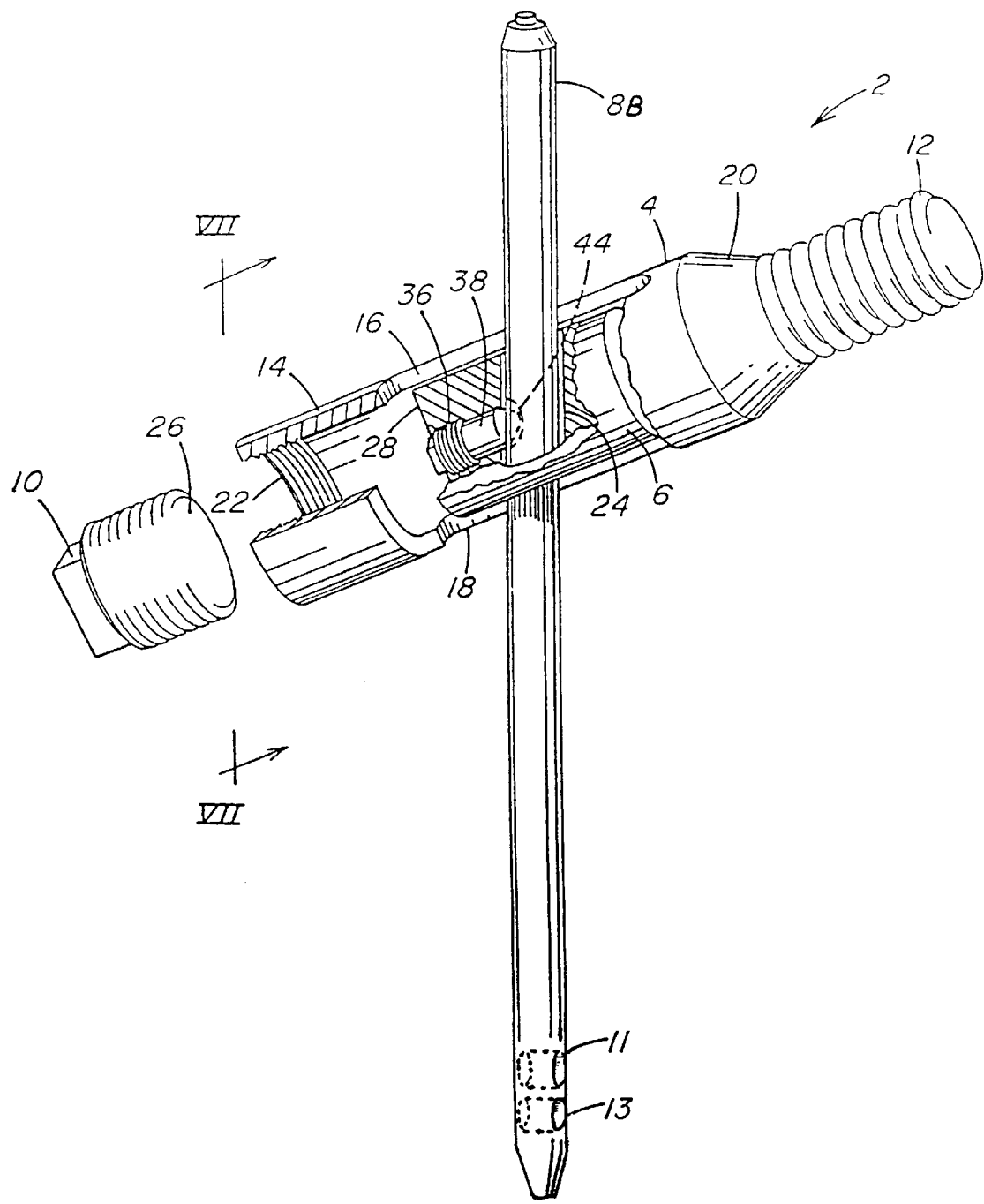

ORTHOPEDIC IMPLANT USED TO REPAIR INTERTROCHANTERIC FRACTURES AND A METHOD FOR INSERTING THE SAME

RELATED APPLICATION

This application claims the benefit under 35 U.S.C. §119(e) of U.S. provisional application No. 60/179,641 filed Feb. 2, 2000.

BACKGROUND OF THE INVENTION

1. Field of the Invention

The present invention relates to a medical device used to repair intertrochanteric fractures of the femur and a method for inserting and using the same.

2. Description of the Currently Available Technology

Current implants for the treatment of intertrochanteric ("IT") fractures consist of a variety of devices which are distinguished by three cardinal features—two of which are generally mechanical in nature and the third of which relates to the surgical procedure for implantation of the devices in a patient.

The femur is generally comprised of its head, which is ball-shaped and fits into the hip socket, its neck which is generally cylindrical in shape and extends from the head of the femur towards the shaft of the femur, the body or shaft of the femur which forms the major longitudinal axis of the femur, and an intermediate region which connects the shaft of the femur with the neck of the femur. This intermediate region is the trochanteric region and, very generally speaking, it holds the body of the femur and the neck of the femur at an angle of about 130 degrees relative to one another. This angle, often called the neck/shaft angle is not always precisely a 130 degree angle, but may vary considerably in each animal or human having a femur, but will generally be referred to hereinafter as a 130 degree angle for discussion purposes. Fractures in the trochanteric region of the femur are generally termed intertrochanteric or "IT" fractures.

All orthopedic implants for the treatment of IT fractures of the femur must operate to hold the head of the femur at the above-described generally 130 degree angle relative to the body of the femur during healing of the fracture of the trochanteric and/or neck of the femur. All such orthopedic implants generally consist of three main elements. The first is a hip implant, also commonly referred to as a hip screw, which is screwed at one end into the head of the femur and extends therefrom to the body of the femur. The second is a stable platform affixed in some manner to the body of the femur. The third is a mechanism for affixing the hip screw and the stable platform to one another in order to hold the body of the femur and the head of the femur at the above-described generally 130 degree angle to one another while the fracture or fractures in the intervening region heals.

The three cardinal features which differentiate the presently available orthopedic implants are: 1) the type of stable platform employed by the implant (e.g., intramedullary or extramedullary); 2) the type of connection between the hip screw and the stable platform (e.g., rigid, dynamic or static plus dynamic); and 3) the surgical procedure, and more particularly, whether it is the hip screw or the stable platform that must be first implanted in the patient.

With regard to the first cardinal feature, there are two types of stable platforms which can be affixed or otherwise associated with the body of the femur—intramedullary and extramedullary. Extramedullary platforms typically employ one or more plates affixed to the outside of the body of the femur with screws which extend generally transverse to the femur's longitudinal axis into the body of the femur to attach the plate to the body of the femur. The hip screw and plate are affixed to one another to hold the head of the femur and the body of the femur at the above-described generally 130 degree angle during the healing process. Extramedullary platforms of this type are particularly useful for nondisplaced or minimally displaced IT fractures.

Intramedullary platforms typically employ an intramedullary nail (IM nail) which is generally a metal rod or tube which is inserted from the top of the femur through the trochanteric region into the hollow core of the body of the femur (known as the intramedullary cavity). The intramedullary nail extends along a portion of the body of the femur, and may extend from the trochanteric region of the femur through nearly all of the body of the femur. The intramedullary nail is generally affixed at its end opposite the end implanted in the trochanteric region (e.g., that portion of the intramedullary nail nearest the patella) to the shaft of the femur with screws inserted transverse to the longitudinal axis of the shaft of the femur through the femur and through the intramedullary nail. The hip screw is positioned generally transverse to the intramedullary nail's longitudinal axis into the head of the femur. The intramedullary nail and hip screw are affixed to one another as explained below, to prevent relative motion in order to provide the stabilization of the body of the femur and the head of the femur at the above described generally 130 degree angle during the healing process.

As between intramedullary platforms and extramedullary platforms, intramedullary platforms are generally more desirable because the moment arm between the head of the femur and the intramedullary nail is less than that of the moment arm of extramedullary platforms where the moment arm extends between the head of the femur and the extramedullary plate attached to the outside of the femur. Thus, the moment arm mechanical forces on the intramedullary implant are lower and it is therefore less likely to experience a mechanical failure. Intramedullary platforms are also desirable because they generally involve a less invasive surgical exposure for implantation. In other words, rather than having to make a surgical incision along a substantial portion of the length of the femur sufficient to permit the surgeon to insert the plate of the extramedullary platform and attach it to the outside of the body of the femur, the intramedullary platform permits the surgeon to simply make a small incision at the top of the femur to insert the intramedullary nail and a small incision on the side of the femur to insert the hip screw.

With regard to the second cardinal feature, the type of connection between the hip screw and the stable platform differentiates presently available orthopedic implants. Such connections may be rigid, dynamic or "static plus dynamic."

Bone compression occurs during the healing process. Bone compression or simply compression, refers here to the process in which bones held together during healing collapse into one another during the healing process to provide a smaller overall dimension than that provided when the fragments were first placed contiguous to one another during the surgery conducted to set the broken bone. Uncontrolled compression is undesirable, but controlled compression is desirable as it permits the fractured bone to heal along desired or required compression paths.

Rigid connections permit no movement in any direction between the stable platform and the hip screw, and are therefor unable to accommodate bone compression that may occur during the healing process.

Dynamic connections permit some movement between the stable platform and the hip screw during the healing process. More particularly, where for example the femur is a human femur and the patient is viewed from a standing position, dynamic connections permit the stable platform to move closer to or further away from the head of the femur along the longitudinal axis of the hip screw, but do not permit vertical movement of the stable platform relative to the longitudinal axis of the hip screw. Dynamic connections can accommodate bone compression, and allow the hip screw to guide the fracture to its most stable position during the healing process without further surgical intervention, but do not provide a post-operative compressive force along the longitudinal axis of the hip screw to urge the stable platform towards the head of the femur, which may be desirable to stabilize the fracture.

Static plus dynamic compression devices also provide such guidance, but permit the surgeon to stabilize the fracture intraoperatively by applying compression forces on the fracture and then allow further dynamic compression during the healing phase.

With regard to the third cardinal feature, the order in which the hip screw and the stable platform are to be surgically implanted differentiates presently available orthopedic implants. More particularly, the design of the orthopedic implant determines the sequence of implantation of the hip screw and the stable platform (e.g., intramedullary nail). In certain intramedullary platforms the hip screw is first inserted, and the stable platform (e.g., intramedullary nail) is then inserted through the hip screw. This type of platform may be referred to as the "hip screw-first" type. In other types, the stable platform (e.g., intramedullary nail) is first inserted followed by insertion of the hip screw. These types may be referred to as "stable platform-first" type.

Hip screw-first designs are desirable because they have a tendency to stabilize the fracture with the hip screw. Subsequent insertion of the stable platform, particularly where the stable platform is an intramedullary nail, is less likely to destabilize or produce unwanted movement of the bone fragments or alignment of the bone fragments. In contrast, stable platform-first designs, particularly where the stable platform is an intramedullary nail, have the potential of causing unwanted distortion of the fracture, unwanted movement of the bone fragments and/or unwanted misalignment of the bone fragments during insertion of the intramedullary nail, which may not and often cannot be corrected upon insertion of the hip screw through the intramedullary nail.

While there are presently available many platforms for the stabilization of the femur to provide for healing of the same for both IT and other femur fractures, there does not exist a platform which: is intramedullary; is capable of providing static plus dynamic compression; and which is of the hip screw-first design, which would therefore combine the best attributes of each into a single orthopedic implant. A need exists in the art for such an intramedullary platform.

SUMMARY OF THE INVENTION

It is an object of the present invention to provide a novel orthopedic implant which is minimally invasive, allows custom fitting of an implant to the dimensions of the femur of a patient, allows for static compression to be applied at the time of surgery as well as allowing for dynamic controlled collapse of the fracture during the healing process and which allows fixation to the shaft of the femur by an intramedullary nail. It is an object of the present invention to provide an orthopedic implant which is intramedullary; is capable of providing static plus dynamic compression; and which is of the hip screw implantation-first design.

These and other objects are obtained with the orthopedic implant of the present invention which includes in cooperation a hip screw, a gliding mechanism, an intramedullary nail, and a compression screw.

The hip screw includes an externally threaded portion for threadable insertion into the head of the femur and a hollow barrel portion, the barrel portion having a pair of opposed slots provided therein along the longitudinal axis of the hip screw. In one embodiment, the hip screw is a hollow tube that tapers from a first diameter to a smaller diameter, the smaller diameter portion having an externally threaded portion to act as a bone screw for insertion into the head of the femur, the larger diameter portion having the slots provided therein. The hollow tube further includes internal or female threads within the barrel portion near the end of the hip screw opposite the bone screw for threadably engaging the compression screw.

The gliding mechanism is generally cylindrical and is retained within the barrel portion of the hip screw with a slidable fit and has a throughhole therethrough transverse of the longitudinal axis of the hip screw. The throughhole is of a diameter which allows a slidable fit with the outside diameter of an intramedullary nail. The throughhole of the gliding mechanism aligns with the slots in the barrel portion of the hip screw to permit the intramedullary nail to pass through the first slot of the barrel portion of the hip screw, through the throughhole of the gliding mechanism and to pass through the second slot of the barrel portion of the intramedullary nail as the intramedullary nail is inserted into the femur through the hip screw and gliding mechanism, whereupon the intramedullary nail is affixed to the gliding mechanism to prevent relative motion between the gliding mechanism and the intramedullary nail.

Upon securing the gliding mechanism to the intramedullary nail, in turn the hip screw and the intramedullary nail are affixed to one another, but due to the slidable fit of the gliding mechanism within the barrel of the hip screw and due to the slots in the hip screw, movement of the gliding mechanism/intramedullary nail assembly along the longitudinal axis of the hip screw can occur as the gliding mechanism glides within the barrel portion of the hip screw.

The internally threaded portion of the barrel portion of the hip screw threadably engages the compression screw, which compression screw is of sufficient length so as to contact the gliding mechanism while the compression screw is still threadably engaged with the internal threads of the barrel portion of the hip screw. Rotating the compression screw further and further into the barrel portion of the hip screw causes the compression screw to urge the gliding mechanism along the longitudinal axis of the hip screw in the direction of the head of the femur, which in turn forces the intramedullary nail in the same direction. Such movement of the intramedullary nail is accommodated by the opposed slots in the barrel portion of the hip screw. As gliding mechanism/intramedullary nail assembly is urged towards the head of the femur, the head of the femur and the body of the femur are caused to be urged toward one another, allowing the surgeon to provide whatever static intra operative compressive force between the body of the femur and the head of the femur is deemed medically necessary. However, as the bone fragments collapse during the healing process, the surgeon can re-operate and rotate the compression screw to provide more compressive force if deemed medically necessary.

In an alternative embodiment of the present invention, the gliding mechanism may be formed of two portions which are joined about the intramedullary nail. While this embodiment introduces additional pieces, it also introduces flexibility in that unlike the above-described embodiment having a throughhole in the gliding mechanism which establishes a fixed angle between the intramedullary nail with respect to the hip screw, the two part embodiment of the gliding mechanism permits any angle between the intramedullary nail and the hip screw, which angle is maintained and secured when the two portions of the gliding mechanism are joined about the intramedullary nail.

The process for the insertion of the orthopedic implant of the present invention is also novel and forms a part of the present invention.

BRIEF DESCRIPTION OF THE DRAWINGS

A complete understanding of the invention will be obtained from the following description when taken in connection with the accompanying drawing figures, wherein like reference characters identified like parts throughout.

FIG. 2 is a front perspective view of one embodiment of the implant of the present invention illustrating a one piece gliding mechanism;

DETAILED DESCRIPTION OF THE PREFERRED EMBODIMENTS

Figure 1A:
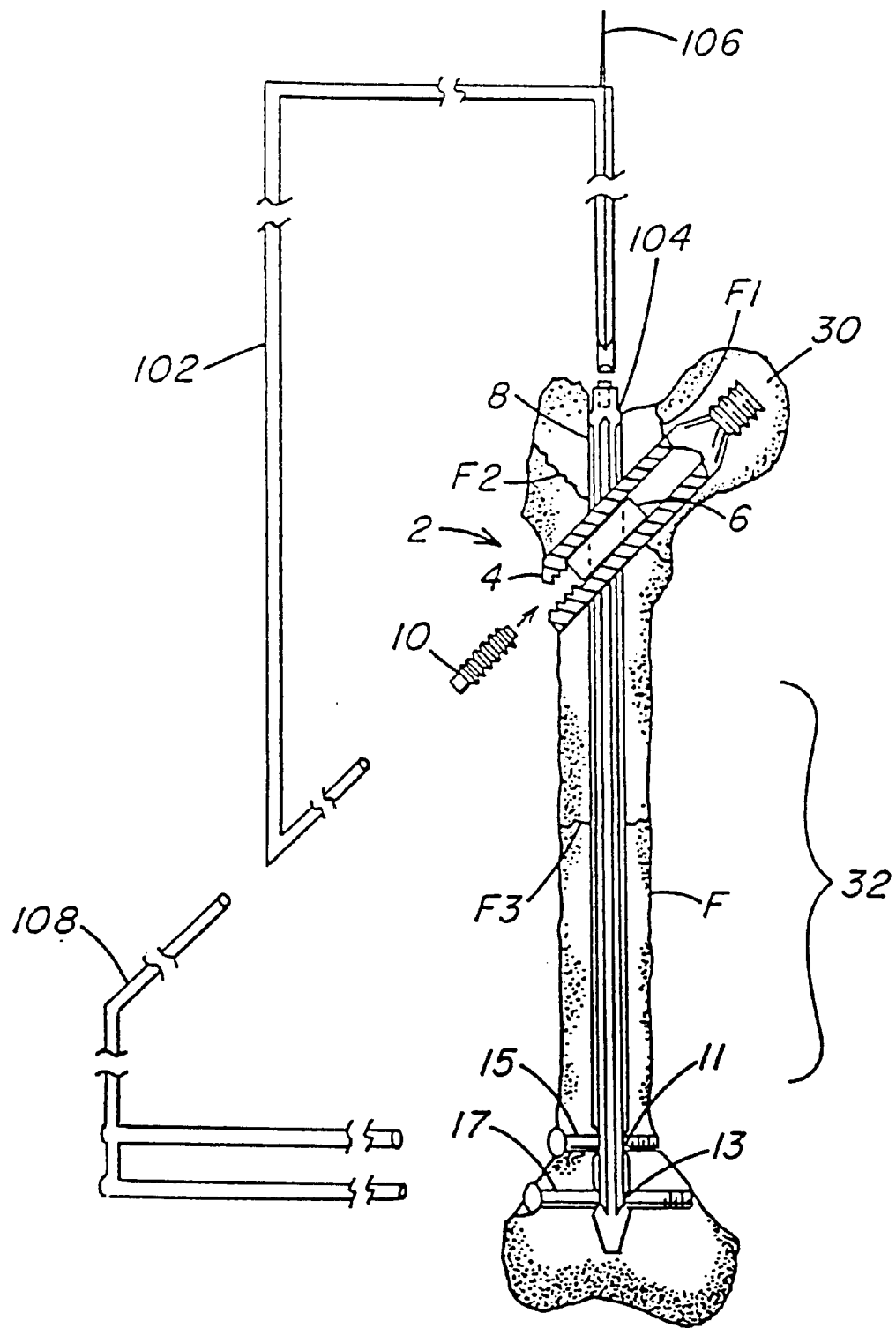
FIG. 1A is a front perspective view of the orthopedic implant of the present invention illustrating the implanting of the implant in a femur.

For purposes of the description hereinafter, the terms "upper", "lower", "right", "left", "top", "bottom" and similar spatial terms shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification are simply exemplary embodiments of the invention. Hence, specific dimensions and other physical characteristics related to the embodiments disclosed therein are not to be considered as limiting. In the following discussion and drawings, like elements are referred to using like reference numerals.

Figure 1B:
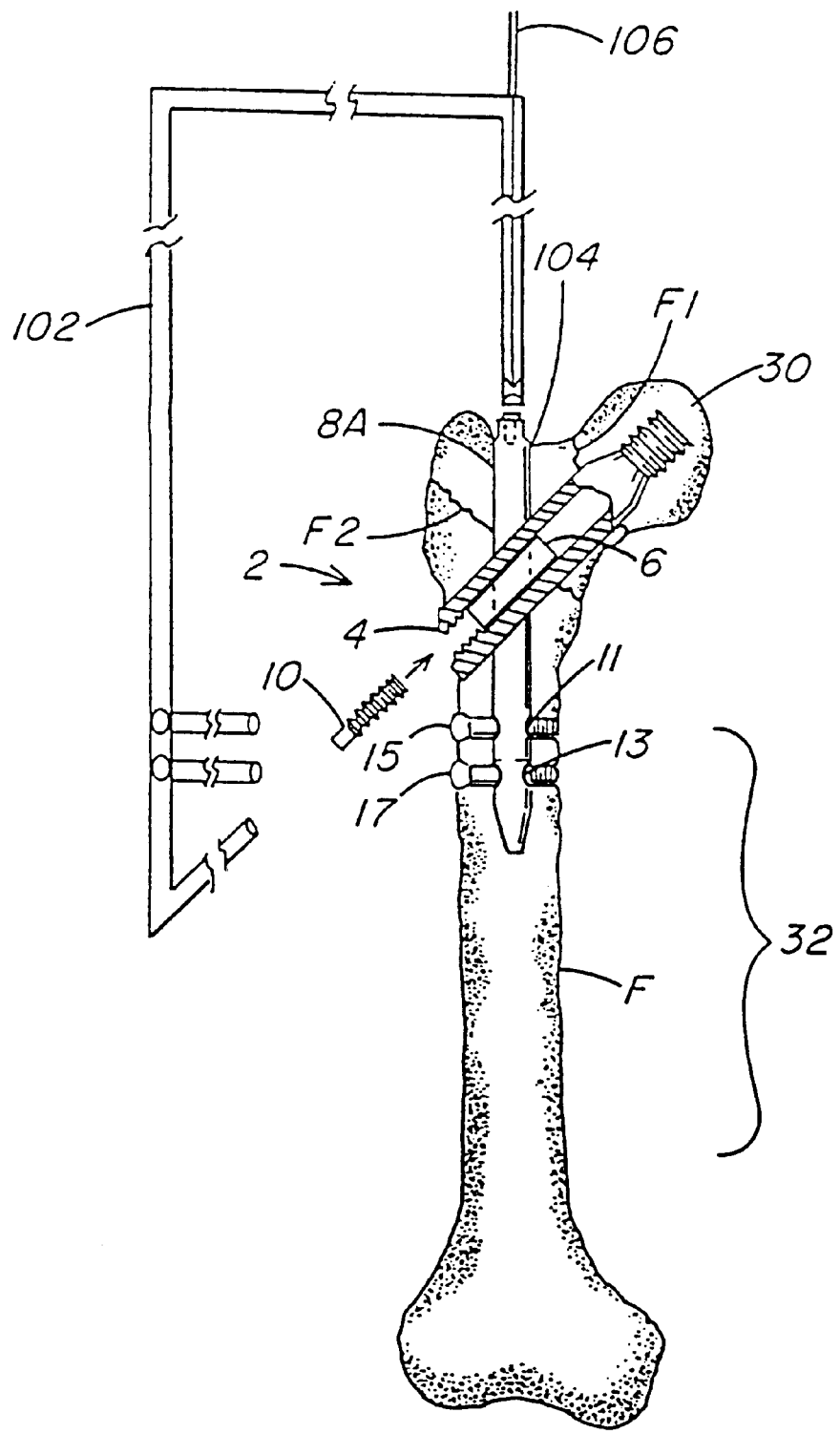
FIG. 1B is a front perspective view of an alternative embodiment of the orthopedic implant of the present invention illustrating the use of a shorter intramedullary nail than is illustrated in FIG. 1A.

Referring now to FIG. 1A, there is illustrated one embodiment of the orthopedic implant of the present invention implanted in femur bone F. Femur bone F is illustrated as having fractures $F_1$, $F_2$, and $F_3$. As may be appreciated, the fractures shown are merely representative, and any fracture pattern may be repaired using the implant of the present invention, however the present invention is particularly well-suited for use in treating fractures of the type of $F_1$ or $F_2$, e.g., fractures of the trochanteric region of the femur as illustrated by $F_2$ or the neck of the femur as illustrated by $F_1$. The orthopedic implant 2 of the present invention includes in cooperation a hip screw 4, a gliding mechanism 6, an intramedullary nail 8, and a compression screw 10. The intramedullary nail 8 may include throughholes 11 and 13 therethrough generally transverse of the longitudinal axis of the intramedullary nail 8 in a portion of the intramedullary nail 8 that is generally opposite that associated with the hip screw 4, hereinafter the distal portion of the intramedullary nail. Set screws 15 and 17 may be inserted into the femur and through the throughholes 11 and 13 respectively to secure the distal portion of the intramedullary nail 8 to the femur F, as illustrated in FIG. 1A.

Where the fracture pattern does not include a fracture of the shaft of the femur (e.g., as exemplified by fracture $F_3$), the intramedullary nail may be considerably shorter as illustrated by intramedullary nail 8A in FIG. 1B.

As may be appreciated, where the fracture pattern includes fractures only of the shaft of the femur F (e.g., as exemplified by fracture $F_3$), such fractures may be treated with only intramedullary nail 8.

Further, the orthopedic implant of the present invention may be utilized even in the absence of fractures of the type of fractures $F_1$, $F_2$, and $F_3$, as for example where the femur is weakened due to a congenital defect or diseased state (e.g., cancer) to provide integral support and/or stabilization for the femur where medically necessary or desirable.

The intramedullary nail 8 illustrated in FIG. 1A is illustrated as a fenestrated or fluted nail. The intramedullary nail 8A illustrated in FIG. 1B is shorter and is illustrated as having a smooth shaft without fenestrations or flutes. Illustrated in FIG. 2 is intramedullary nail 8B which is illustrated as a long intramedullary nail without fenestrations or flutes. Illustrated in FIGS. 3A through 5B are other modified intramedullary nails 8C through 8J which depict other embodiments of the intramedullary nail of the present invention. Nails 8 through 8J may each be used in connection with the present invention and hereinafter reference to any of intramedullary nails 8 through 8J shall include all embodiments of the intramedullary nail unless otherwise clear from the content of use. In embodiments not illustrated herein, portions of intramedullary nails 8 through 8J may be fenestrated while portions are not. For example, intramedullary nails 8 through 8J may be fenestrated in areas other than in the general proximity of the hip screw 4, while the area of the respective intramedullary nail in the proximity of the hip screw 4 is not fenestrated.

Referring now to FIG. 2, the hip screw 4 includes an externally threaded portion 12 for threadable insertion into the head of the femur and a hollow barrel portion 14, the barrel portion having a pair of opposed slots 16, 18 provided therein along the longitudinal axis of the hip screw 4. As may be appreciated, the threaded portion 12 is not limiting to the invention, and any mechanism known or hereinafter developed which will secure the hip screw 4 into the head of the femur is within the scope of the present invention, which may include but is not limited to friction or press fit mechanisms as opposed to or in conjunction with a threadable engagement with the head of the femur.

In one embodiment of the present invention, the hip screw 4 includes hollow tube portion 14 which tapers from a first diameter to a smaller diameter as illustrated by taper region 20, the smaller diameter portion having the externally threaded portion 12 to act as a bone screw for insertion into the head of the femur, the larger diameter portion 14 having the slots 16 and 18 provided therein. The hollow tube portion 14 further includes internal or female threads 22 within the barrel portion 14 near the end of the hip screw 4 opposite the externally threaded portion 12.

In one embodiment, the gliding mechanism 6 is generally cylindrical and is retained within the barrel portion 14 of the hip screw 4 with a slidable fit and has a throughhole 24 therethrough transverse of the longitudinal axis of the gliding mechanism 6. The throughhole 24 is of a diameter which allows a slidable fit with the outside diameter of the intramedullary nail 8B. The throughhole 24 of the gliding mechanism 6 aligns with the slots 16 and 18 in the barrel portion 14 of the hip screw 4 to permit the intramedullary nail 8B to pass through the first slot 16 of the barrel portion 14 of the hip screw 4, through the throughhole 24 of the gliding mechanism 6 and to pass through the second slot 18 of the barrel portion 14 of the hip screw 4 as the intramedullary nail 8B is inserted into the femur through the hip screw 4 and gliding mechanism 6, whereupon the intramedullary nail 8B is affixed to the gliding mechanism 6 to prevent relative motion between the gliding mechanism 6 and the intramedullary nail 8B as described hereinafter.

Upon securing the gliding mechanism 6 to the intramedullary nail 8B, in turn the hip screw 4 and the intramedullary nail 8B are affixed to one another, but due to the slidable fit of the gliding mechanism 6 within the barrel portion 14 of the hip screw 4 and due to the slots 16 and 18 in the hip screw 4, movement of the gliding mechanism 6/intramedullary nail 8B assembly along the longitudinal axis of the hip screw 4 can occur as the gliding mechanism 6 glides within the barrel portion 14 of the hip screw 4.

The internally threaded portion 22 of the barrel portion 14 of the hip screw 4 threadably engages the compression screw 10. Preferably, the compression screw 10 is of sufficient length so as to contact the gliding mechanism 6 while the compression screw 10 is still threadably engaged with the internal threaded portion 22 of the barrel portion 14 of the hip screw 4. More particularly, the surface 26 of the compression screw 10 contacts the surface 28 of the gliding mechanism 6 as the compression screw 10 is threaded into threaded portion 22 in the barrel portion 14 of the hip screw 4. Rotating the compression screw 10 further and further into the barrel portion 14 with threaded portion 22 of the hip screw 4 causes the compression screw 10 to urge the gliding mechanism 6 further and further along the longitudinal axis of the hip screw 4 in the direction of the head of the femur, which in turn forces the intramedullary nail 8B in the same direction. Such movement of the intramedullary nail 8B is accommodated by the opposed slots 16 and 18 in the barrel portion 14 of the hip screw 4. As the gliding mechanism 6/intramedullary nail 8B assembly is urged towards the head of the femur, the head of the femur 30 and the body of the femur 32 are caused to be urged toward one another, allowing the surgeon to provide whatever static post operative compressive force between the body of the femur 32 and the head of the femur 30 is deemed medically necessary. However, as the bone fragments collapse into one another during the healing process, the surgeon can continue to rotate the compression screw 10 to provide more and more compressive force if deemed medically necessary. In short, the surgeon is provided with complete control over the amount of compressive force to be applied by operation of the compression screw 10 in the manner just described.

Figure 3A:
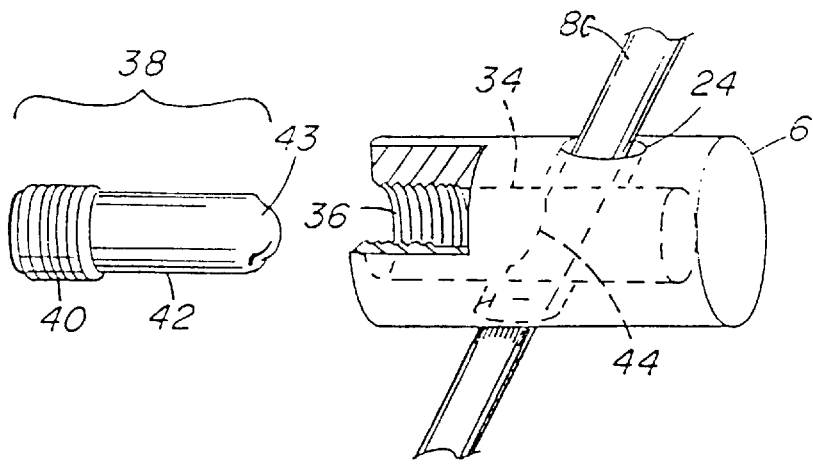
FIGS. 3A, 3B and 3C are front perspective views illustrating alternative embodiments for affixing the intramedullary nail to the gliding mechanism of the present invention.

In one embodiment illustrated in FIGS. 2 and 3A, gliding mechanism 6 is provided with bore 34 which extends along the longitudinal axis of the gliding mechanism 6 from the surface 28 to the throughhole 24 and is preferably generally centrally located along the longitudinal axis of the gliding mechanism 6. The bore 34 is provided with internal threads 36 which threadably engage set screw 38. Set screw 38 includes treaded portion 40 and locking portion 42 and projection 43. In the embodiment illustrated in FIG. 2, the intramedullary nail 8B (and in FIG. 3A the intramedullary nail 8C) includes a recess 44 which is adapted to receive projection 43 of set screw 38. Threadable insertion of the set screw 38 into the recess 44 prevents relative motion between the intramedullary nail 8B or 8C and the gliding mechanism 6.

Figure 3B:
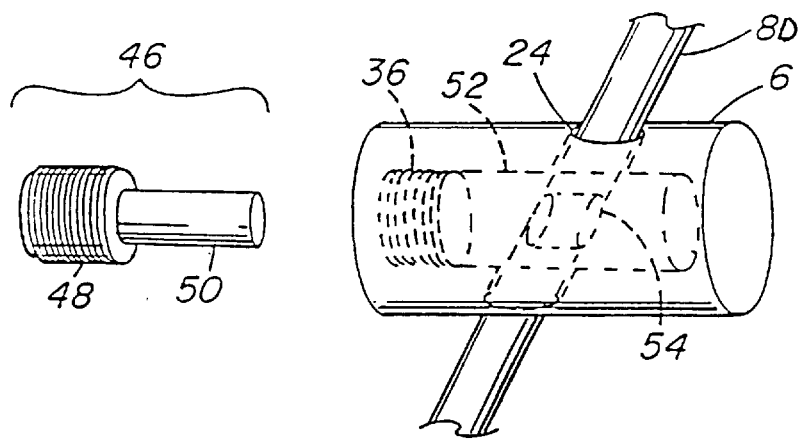

As may be appreciated, the present invention is not limited to the embodiment of set screw 38 illustrated in FIGS. 2 and 3A and other embodiments that prevent relative motion between the intramedullary nail and the gliding mechanism 6 may be employed. Another example is illustrated in FIG. 3B, where set screw 46 is shown, which includes threaded portion 48 and cylindrical portion 50 which does not include a projection. Gliding mechanism 6 includes bore 52 having internal threaded portion 36, however, bore 52 differs from bore 34 in that it extends beyond throughhole 24 into that portion of gliding mechanism 6 that is on the far side of the throughhole 24. Intramedullary nail 8D in this embodiment includes throughhole 54 therethrough, which throughhole 54 provides a slidable fit with the exterior surface of cylinder portion 50 of set screw 46. In this embodiment, as the set screw 46 is threadably inserted it passes through throughhole 54 and into the far side of the bore 52, whereupon relative motion of the intramedullary nail 8D and the gliding mechanism 6 is prevented.

Figure 3C:
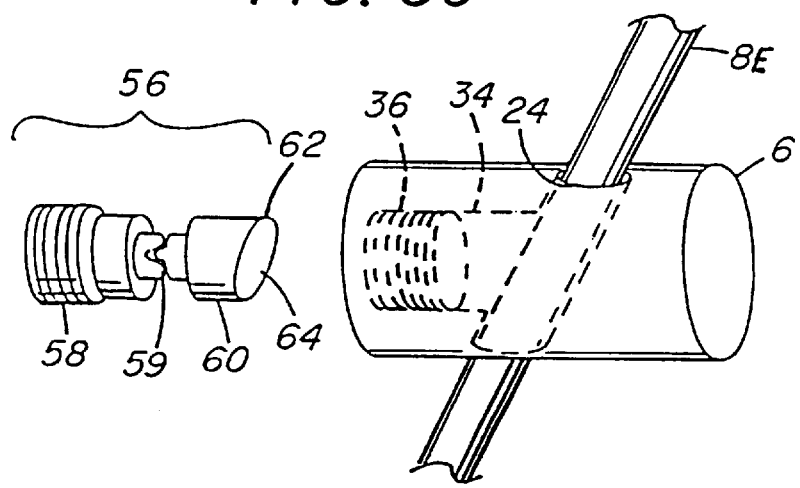

In yet another embodiment illustrated in FIG. 3C, the set screw 56 includes threaded portion 58 connected by swivel device 59 to cylindrical portion 60, which cylindrical portion 60 terminates at an angle 62 to provide a surface 64 which is generally parallel with the longitudinal axis of the intramedullary nail 8E. The swivel 59 functions to permit the surface 64 to maintain alignment with intramedullary nail 8E as the set screw 56 is tightened in bore 34. Bore 34 having internal threads 36 is again provided, as described above. In this embodiment, as the set screw 56 is inserted into the bore 34, surface 64 is brought to bear on intramedullary nail 8E preventing relative motion between the intramedullary nail 8E and the gliding mechanism 6. One advantage of the embodiment of 3C is that any standard intramedullary nail may be employed, and such standard intramedullary nail need not have either recess 44 of FIG. 3A or throughhole 54 of FIG. 3B therein.

The embodiments illustrated in FIGS. 3A through 3C are only exemplary, and other embodiments of such a set screw not illustrated may be employed as within the scope of the present invention. For example, the set screw may be provided of the type of set screw 38 but with a simple rounded end portion as opposed to a projection or angled portion, which upon tightening in the threads 36 will similarly prevent relative motion between the gliding mechanism 6 and the intramedullary nail 8.

Figure 4A:
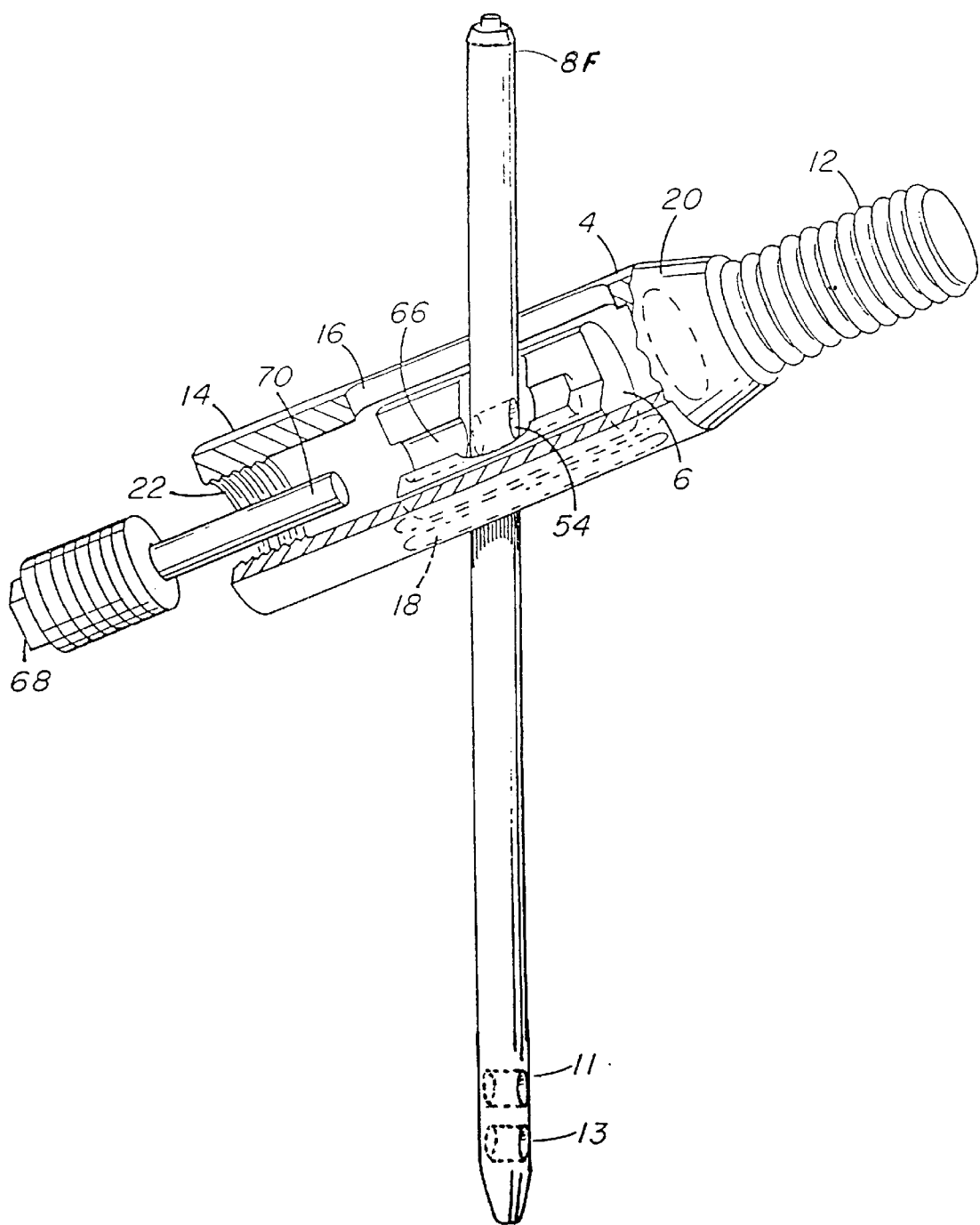
FIG. 4A is a front perspective view of yet another embodiment for affixing the intramedullary nail to the gliding mechanism of the present invention.

Illustrated in FIG. 4A is yet another embodiment of the present invention where the set screw is replaced with a modified compression screw. Referring now to FIG. 4A, there is illustrated hip screw 4 and intramedullary nail 8F however, in this embodiment the gliding mechanism 6 includes bore 66 which is similar to bore 52 of FIG. 3B, but does not include internal threaded portion 36. The compression screw 68 includes locking pin 70 integrally formed therewith. As the compression screw 68 is threadably engaged into threaded portion 22 of the barrel portion 14 of the hip screw 4, the locking pin 70 is inserted into the bore 66 of the gliding mechanism 6, and passes through throughhole 54 in intramedullary nail 8F. The exterior diameter of the locking pin 70 and the internal diameter of the bore 66 and throughhole 54 are preferably selected so as to provide a close but slidable fit. Upon insertion of the locking pin 70 into the bore 66 of the gliding mechanism 6 and through the throughhole 54 of the intramedullary nail 8F, the intramedullary nail 8F and the gliding mechanism are affixed to one another by the locking pin 70 to prevent relative motion between the gliding mechanism 6 and the intramedullary nail 8F.

Generally speaking with respect to all embodiments discussed and/or illustrated above, the hip screw sliding mechanism, intramedullary nail, compression screw 10 and set screw (when present) may be formed of any material that is biologically compatible with the animal into which the device is inserted and which can withstand the stresses provided by that animal during the healing process. The term animal as used herein includes but is not limited to humans. Polymeric materials may be used. Metals, including but not limited to stainless steel or titanium metals or alloys or any other biologically inert materials may also be used, as well as combinations thereof wherein some or all of one or more of the components are formed of a polymeric material while others are formed of metals. In a particularly preferred embodiment of the present invention, all of the components are formed of surgical grade stainless steel.

Figure 4B:
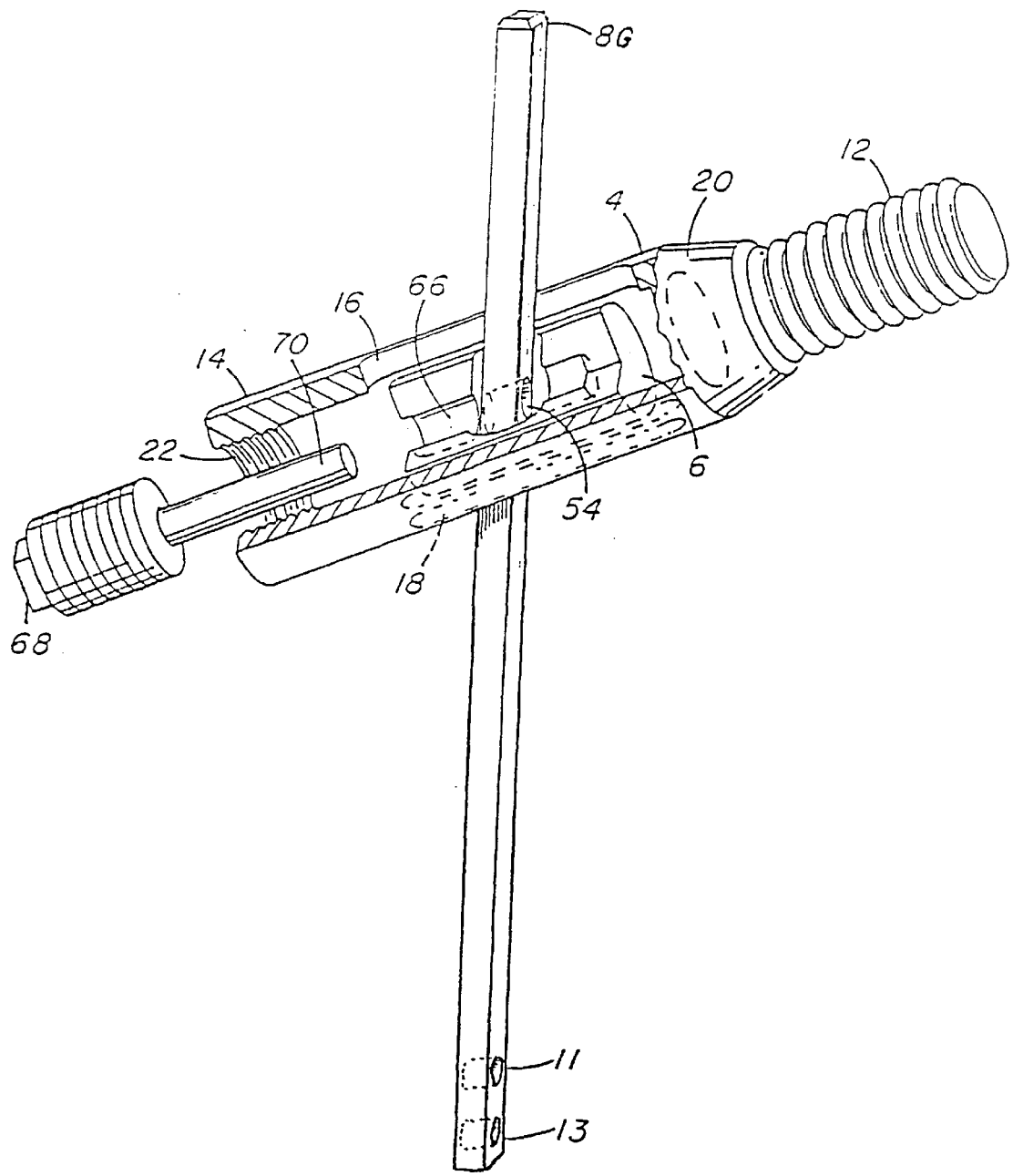
FIGS. 4B and 4C are front perspective views illustrating alternative embodiments of the intramedullary nail.
Figure 4C:
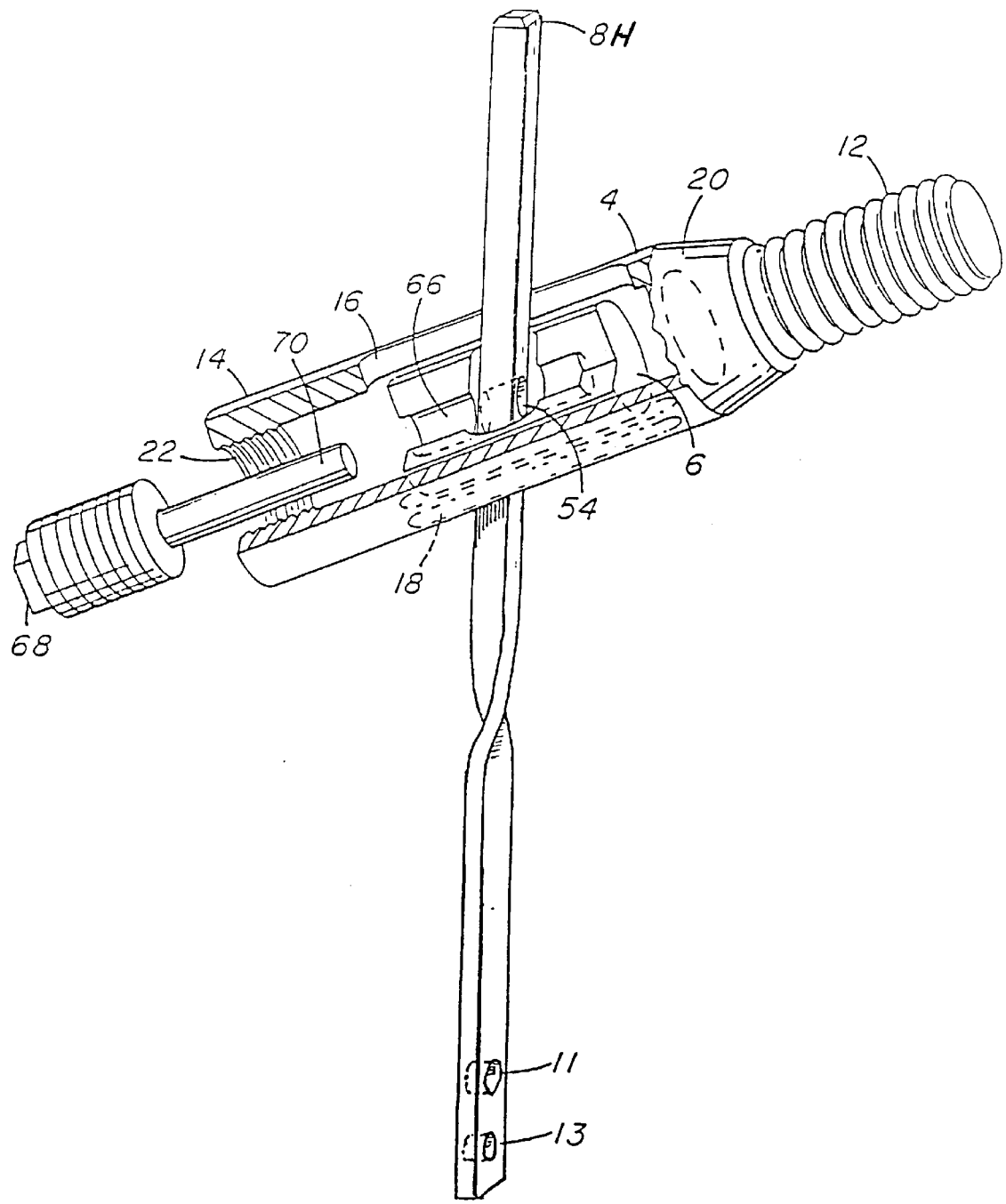

Referring now to FIGS. 4B and 4C, there are illustrated alternative embodiments of the intramedullary nail. FIG. 4B illustrates an embodiment in which intramedullary nail 8G has a square or rectangular cross section. In alternative embodiments not illustrated, the intramedullary nail may have cross sections of other geometric shapes, for example, and without limiting the invention, oval, elliptical, hexagonal, or octagonal. In such alternative embodiments, the intramedullary nail may have the same cross section for its entire length, or the shape or dimensions of the cross section may vary along the length of the intramedullary nail. All such alternative embodiments are within the scope of the present invention.

FIG. 4C illustrates an embodiment in which intramedullary nail 8H has a square or rectangular cross section and is twisted along its longitudinal axis. Twisting the intramedullary nail 8H in this way increases its structural rigidity. Such twisting is particularly advantageous in embodiments wherein the intramedullary nail 8H has a rectangular, elliptical or oval cross section. In such embodiments, it may be preferable or necessary to insert the intramedullary nail 8H through hip screw 4 and gliding mechanism 6 such that the longest cross sectional dimension of the intramedullary nail 8H is generally aligned with the longitudinal axis of hip screw 4 and gliding mechanism 6. In such cases, it is generally preferable to position throughholes 11 and 13 on the widest surfaces of intramedullary nail 8H wherein the throughholes 11 and 13 pass through the narrower cross sectional dimension of intramedullary nail 8H. Twisting intramedullary nail 8H 90 degrees (or 90 degrees plus any multiple of 180 degrees) along its longitudinal axis in such embodiments allows throughholes 11 and 13 to be oriented such that set screws (not shown) may be easily inserted from the side of the femur in the manner illustrated in FIGS. 1A and 1B.

FIG. 4C illustrates an embodiment of intramedullary nail 8H wherein said intramedullary nail 8H is twisted 90 degrees, with the twist occurring over a relatively short section of the length of intramedullary nail 8H. FIG. 4C is exemplary only. To minimize the potential for the twisted portion of intramedullary nail 8H to bind during insertion through the hip screw 4 and the gliding mechanism 6, it is preferable for the twisting to occur more gradually over the entire length of the intramedullary nail 8H. Embodiments having more or less twisting or more gradual or less gradual twisting than that illustrated in FIG. 4C are all within the scope of the present invention. Likewise, any degree of twisting of intramedullary nail 8H (including, without limitation, twisting more than 360 degrees) is within the scope of the present invention.

The alternative embodiments of the intramedullary nail illustrated in FIGS. 4B and 4C are illustrated with throughhole 54 for insertion of locking pin 70. However, these illustrations are exemplary only and are not limiting. As may be appreciated, such alternative embodiments of the intramedullary nail may also be designed for use in other embodiments of the invention described herein that do not employ throughhole 54 or locking pin 70.

In the foregoing embodiments illustrated in FIGS. 1 through 4C, the intramedullary nail 8 through 8H passed through the gliding mechanism 6 at an angle fixed by the throughhole 24 in the gliding mechanism 6. However, in an alternative embodiment of the present invention, the gliding mechanism may be formed of two portions which are joined about the intramedullary nail. Each such portion may form generally about half of the gliding mechanism 6, but the invention is not so limited and either portion may comprise more than half of the gliding mechanism 6. While this embodiment introduces additional pieces (e.g., a two-piece gliding mechanism as opposed to the above described single piece gliding mechanism), it also introduces greater flexibility in that unlike the above-described embodiment having a throughhole 24 in the gliding mechanism 6 which establishes a fixed angle between the intramedullary nail 8 with respect to the hip screw 4. The two-piece embodiment of the gliding mechanism of the present embodiment permits any angle between the intramedullary nail and the hip screw, which angle is maintained and secured when the two portions of the gliding mechanism are joined about the intramedullary nail as illustrated in FIGS. 5A, 5B and 6.

Figure 5A:
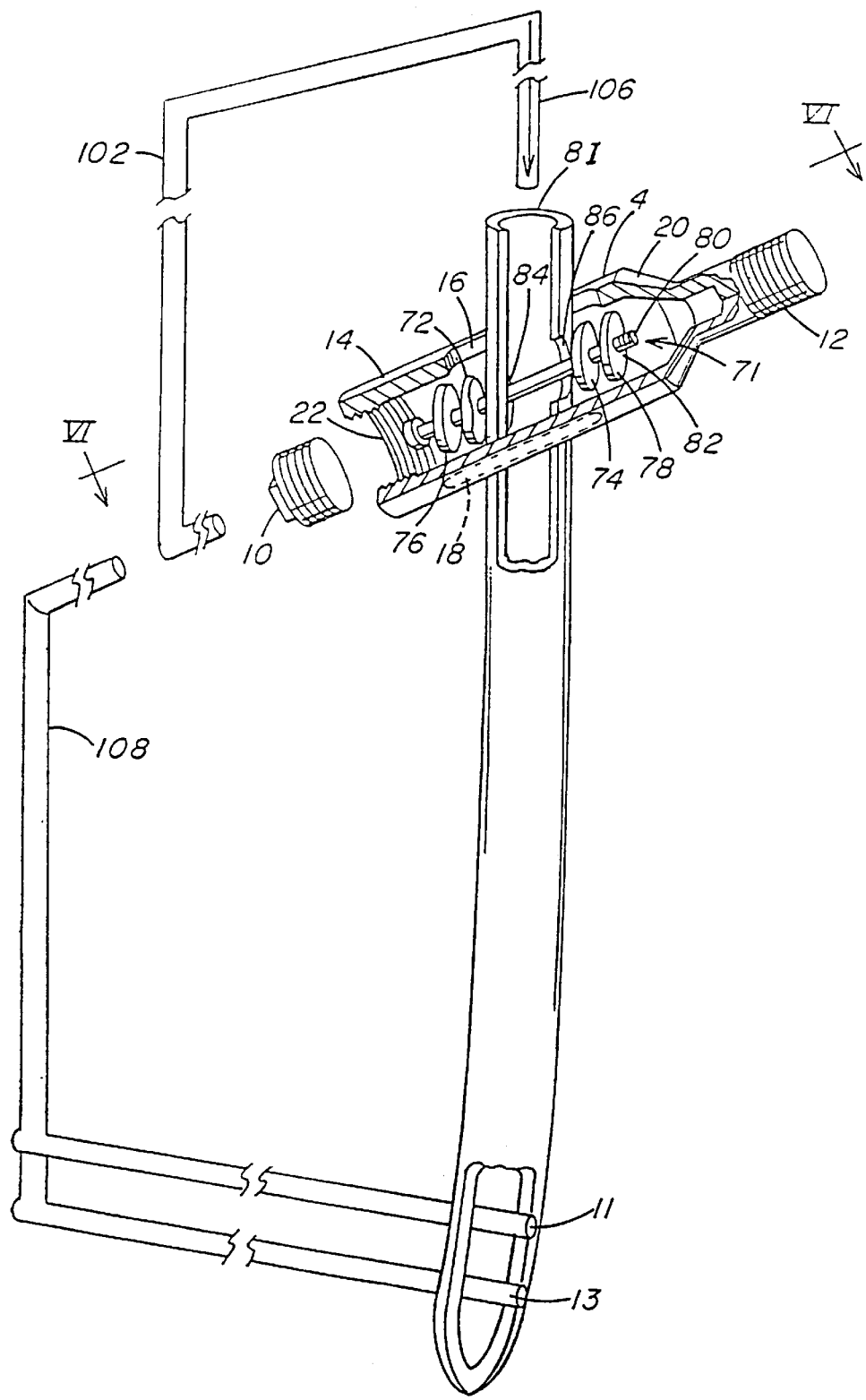
FIG. 5A is a front perspective view of a two-piece gliding mechanism in accordance with the present invention.
Figure 5B:
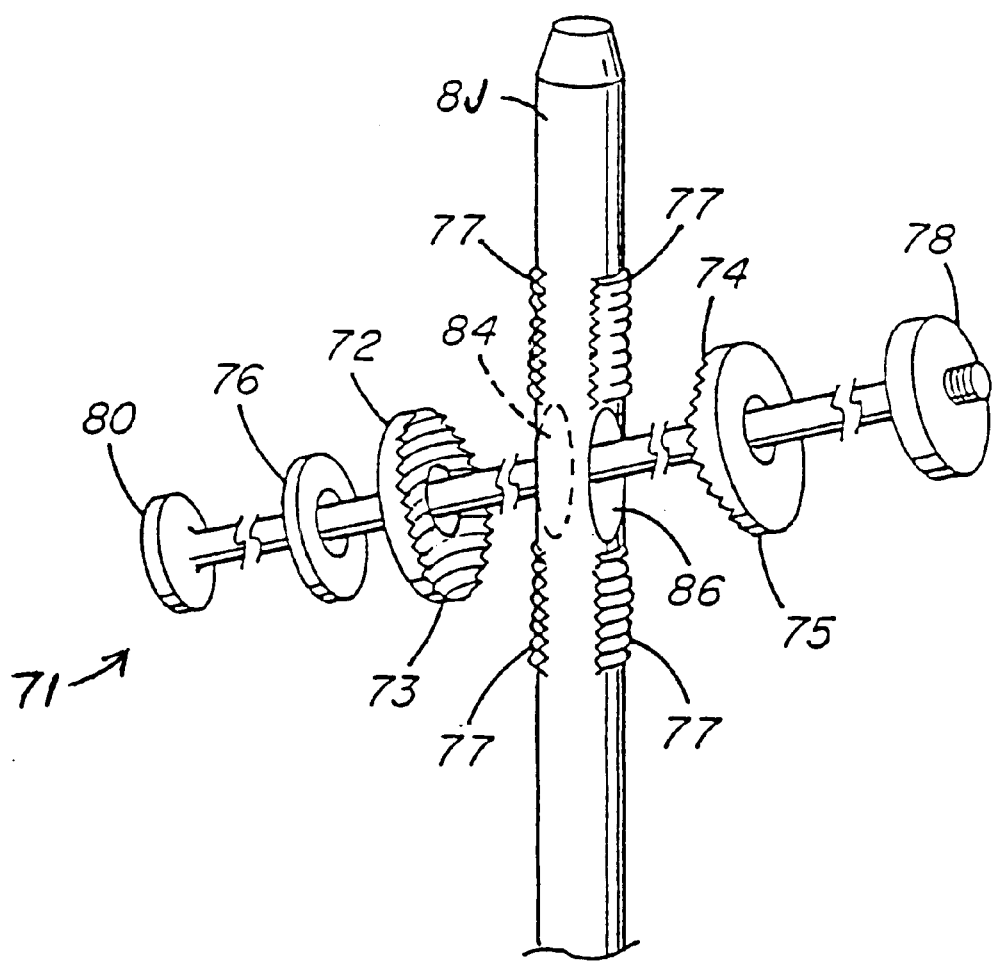
FIG. 5B is a front perspective view of an alternative embodiment of the two-piece gliding mechanism illustrating an intramedullary nail with a notched surface and a gliding mechanism having a pair of toothed washers which interlock with the notched surface of the intramedullary nail.
Figure 6:
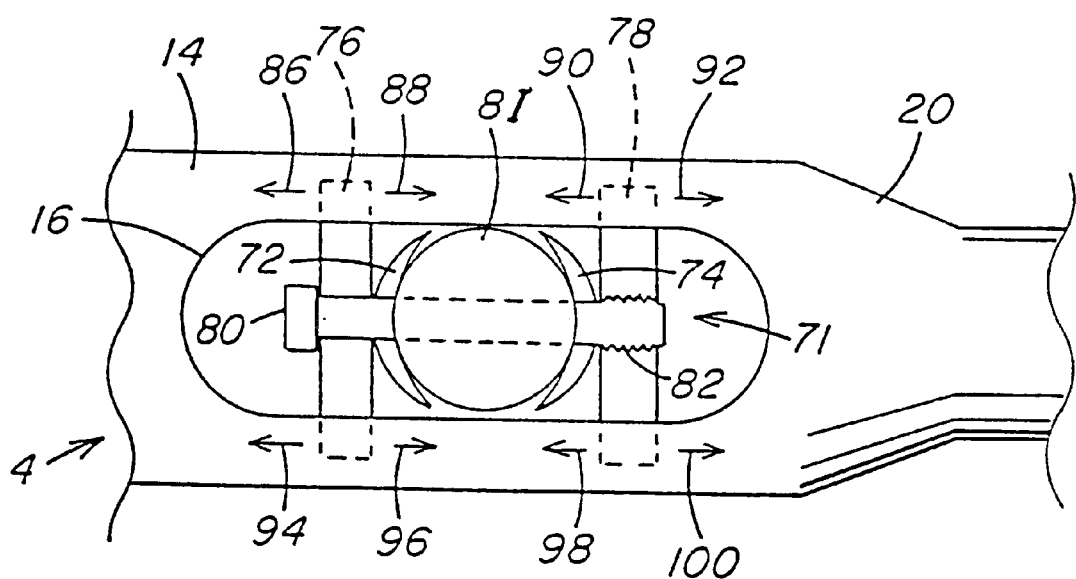
FIG. 6 is a partial top plan view of the barrel portion of the two-piece gliding mechanism of FIG. 5A.

Referring now to FIGS. 5A, 5B and 6 there is illustrated hip screw 4 and intramedullary nail 8I which are connected to one another through a two-portion gliding mechanism 71. FIG. 6 is a top plan view taken along the line VI—VI of FIG. 5A. The hip screw 4 is provided with the same threaded portion 12, barrel portion 14, tapered section 20, and pair of opposed slots 16 and 18 as described above. Also illustrated in FIG. 5A is the compression screw 10 and the internal threaded portion 22 in the barrel portion 14 of the hip screw 4. As may be appreciated, the compression screw 10 (or compression screw 68) are optional, but preferable elements of the present invention.

As shown in FIGS. 5A and 6, the intramedullary nail 8I is supported within the hip screw 4 with a plurality of compression members such as a first washer 72, a second washer 74, a first bushing 76, a second bushing 78, and a force applying device such as a screw 80. The first bushing 76, the first washer 72 and the second washer 74 each have a central bore configured to permit the screw 80 to pass therethrough. The second bushing 78 has internal threads 82 along at least a portion of its central bore and the screw 80 has complementary threads on the exterior surface thereof for threadable engagement of the screw 80 with the second bushing 78. The first washer 72, second washer 74, first bushing 76, second bushing 78 and screw 80 collectively form the two part gliding mechanism 71 of this embodiment of the present invention. More particularly, the first washer 72 and first bushing 76 form the first part of the gliding mechanism 71 and the second washer 74 and the second bushing 78 for the second part, which parts are affixed to one another about the intramedullary nail 8I by the screw 80. The screw 80 passes through the first bushing 76, the first washer 72, the intramedullary nail 8I, the second washer 74 and the second bushing 78 and upon tightening pulls the two portions together around the intramedullary nail 8I. The intramedullary nail 8I may be provided a throughhole (not shown), through which screw 80 passes as it is being inserted through the bushings and washers, which throughhole may be provided generally perpendicular to the longitudinal axis of the intramedullary nail 8I or may be at an angle to provide a desired angle of the intramedullary nail 8I with the hip screw 4. In an alternative embodiment, the intramedullary nail 8I may be provided with slots 84 and 86 which extend along the longitudinal axis of the intramedullary nail in the area where the screw 80 passes through the intramedullary nail. Slots 84 and 86 permit the intramedullary nail 8I and the hip screw 4 to be positioned at any angle relative to one another, which angle is then retained upon tightening the screw 80.

Illustrated in FIG. 5B is a front perspective view of an alternative embodiment of the two-piece gliding mechanism illustrating teeth 73 and 75 on the surfaces of washers 72 and 74 respectively adjacent the intramedullary nail 8J which lock into corresponding notches 77 on the exterior surface of intramedullary nail 8J. The teeth 73 and 75 interlock with the notches 77 to permit the angle at which the screw 80 passes through intramedullary nail 8J to be maintained after tightening of the two halves of the gliding mechanism 71 about the intramedullary nail 8J after the screw 80 is passed through slots 84 and 86 in the intramedullary nail 8J. As may be appreciated, the present invention is not limited to the teeth/notch assembly illustrated in FIG. 5B, but may include any device which provides an interlock between the washers and the intramedullary nail.

In a preferred embodiment, the bushings 76 and 78 are larger in diameter than the diameter of the intramedullary nails 8I or 8J. The internal diameter of the barrel portion 14 of the hip screw 4 is substantially the same diameter of the bushings 76 and 78 to provide a slidable fit of the bushings 76 and 78 in the barrel portion of the 14 of the hip screw 4. The pair of opposed slots 16 and 18 in the barrel portion 14 of the hip screw 4 are approximately the same width (width here referring to the measurement of the slot transverse of the longitudinal axis of the hip screw) as the outside diameter of the intramedullary nail 8I or 8J to permit a slidable fit of the intramedullary nail 8I or 8J through the slots 16 and 18. As noted above, the intramedullary nail 8I or 8J may be further secured to the femur by one or more distal locking screws (not shown) which are fitted through the distal apertures 11 and 13, respectively.

The hip screw 4, the intramedullary nail 8I or 8J, and the screw 80 may be made of metal, polymeric materials or any other resilient material that is biologically compatible with the animal into which the orthopedic implant is used and which can withstand the stresses placed by that animal on the implant. Preferably, the hip screw 4, the intramedullary nail 8I or 8J, the screw 80 and the bushings 76 and 78 are made of stainless steel or a titanium alloy. The washers 72, 74 may be made of the above-described metal or polymeric materials, but are preferably made of the same material as the rest of the orthopedic implant.

As can be seen by the directional arrows 86, 88, 90, 92, 94, 96, 98, and 100 illustrated in FIG. 6, the orthopedic implant of this embodiment of the present invention provides for settlement or collapse of the bone fragments in the IT region which commonly occurs as the bone fragments fuse to one another during the healing process, as the gliding mechanism comprised of the washers 72, 74, bushings 76, 78 and screw 80 can slide in a generally horizontal direction in the barrel portion 14 of the hip screw 4 along the longitudinal axis of the hip screw due to the pair of opposed slots 16 and 18 provided in the hip screw 4 which permits lateral movement of the hip screw 4. Where no compression screw of the type of compression screws 10 and 68 are provided, this lateral movement may occur in a floating fashion. Where a compression screw is employed, this lateral movement may be controlled using the compression screw as described above.

The design of the orthopedic implant illustrated in FIGS. 5A, 5B and 6 permits the angle between the hip screw 4 and the intramedullary nail 8I or 8J to be varied by the surgeon to any desired angle and then locked at that angle by tightening the screw 80. This in turn provides for custom fitting of the orthopedic implant to the patient's anatomy. During the healing process, the intramedullary nail 8I or 8J can slide relative to the hip screw 4 via the gliding mechanism 71 to accommodate but control the direction of collapse of the fracture during the healing process.

In an embodiment not shown, the intramedullary nail, when in the form of a hollow tube, may be fitted with an internal cage nut or similar nut on its interior surface to threadably engage screw 80. Where the intramedullary nail includes such an internal cage nut, the screw 80 need only be of sufficient length so as to extend from first bushing 76 to the internal cage nut, and second washer 74 and the second bushing 78 may be dispensed with if desired. As with the embodiments described above, the use of a compression screw of the type of compression screw 10 may be optionally, but preferably employed.

Figure 7A:
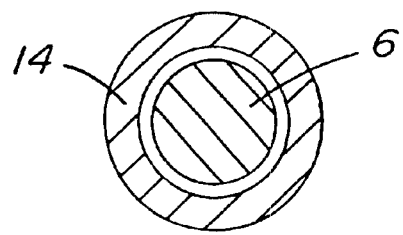
FIGS. 7A, 7B, 7D and 7C are sectional views along the line VII—VII of FIG. 2 illustrating alternative embodiments of the cross sections for the barrel and gliding mechanism of the present invention.
Figure 7B:
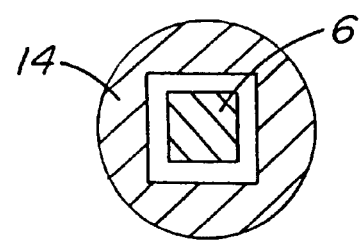
Figure 7C:
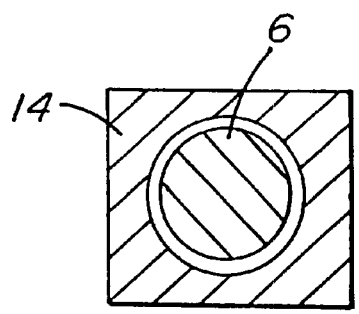
Figure 7D:
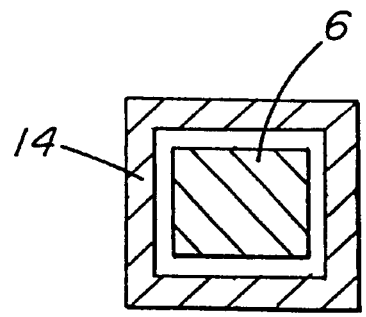

In all of the embodiments illustrated and described above in FIGS. 1–6, the barrel portion 14 of the hip screw 4 has been shown generally cylindrical in shape, and the gliding mechanisms 6 and 71 (particularly the bushings and washers of gliding mechanism 71) have been illustrated as generally cylindrical in shape. However, the invention is not so limited. As may be appreciated, various configurations of the barrel portion 14 and the gliding mechanism 6 may be employed as within the scope of the present invention, including but not limited to those illustrated in FIGS. 7A–7D. Illustrated in FIG. 7 are several embodiments which conform to a view generally taken along the line VII—VII in FIG. 2. Illustrated in FIG. 7A is a generally cylindrical barrel portion 14 and generally cylindrical gliding mechanism 6. Illustrated in FIG. 7B is a generally cylindrical barrel portion 14 and a generally square or rectangular gliding mechanism 6. Illustrated in FIG. 7C is a generally square or rectangular barrel portion 14 and a generally cylindrical gliding mechanism 6. Illustrated in FIG. 7D is a generally square or rectangular barrel portion 14 and a generally square or rectangular gliding mechanism 6. The present invention is not limited to these combinations, and any geometric combination which permits gliding mechanism 6 to slide within a barrel portion 14 may be employed as within the scope of the present invention. Where the generally square or rectangular barrel portion is used, it is preferable that the externally threaded portion 12 is replaced with a press fit design for insertion of the hip screw into the head of the femur to avoid the need for rotating the barrel portion upon its insertion through the shaft of the femur into the head of the femur. Also as may be appreciated, where a square or rectangular barrel portion is used, the hole through the femur may also be square or rectangular to provide a slidable fit of the square or rectangular barrel through the shaft of the femur, particularly where the externally threaded portion 12 has been replaced with a press fit design as described above.

The surgical procedure for implanting the orthopedic implant of the present invention will now be described. The following discussion will describe the surgical procedure when using either the fixed angle gliding mechanism 6 (illustrated in FIGS. 1–4 and described in the related discussion) and the two part variable angle gliding mechanism 71 (illustrated in FIGS. 5A, 5B and 6 described in the related discussion).

The fracture in the intertrochanteric region is reduced in the manner preferred by the surgeon, but will typically involve longitudinal traction, internal rotation and abduction of the leg. The surgical field is then prepared in the standard fashion.

An incision is made on the lateral hip in line with the central axis of the femoral neck. A guide pin is inserted from the lateral border of the femur and advanced precisely along the central axis of the femoral neck into the femoral head. A drill having a diameter adapted to provide a threadable fit for the threaded portion 12 of the hip screw 4 is then inserted over the guide pin and a bore is made into the head of the femur 30. The drill is removed, and the hip screw 4 is then inserted. In one embodiment the guide pin may simply be removed to accommodate the hip screw 4. However, in a preferred embodiment, the hip screw 4 is provided with a bore through the threaded portion 12 (which bore is not shown) to permit the hip screw 4 to be advanced over the guide pin. In either case, the threaded portion 12 is threadably engaged into the bore in the head of the femur until the hip screw 4 is fully seated into the head of the femur and the hip screw 4 is positioned so the opposed slots 16 and 18 are in line with the shaft of the femur. If not previously removed, the guide pin is then removed. By this method in which the hip screw 4 is implanted prior to the implantation of the intramedullary nail 8, the fracture is provisionally stabilized and the leg can be repositioned if necessary to progress onto the next step. This will be necessary more often in an obese patient or in one which required extreme positioning measures to achieve adequate reduction.

A first guide assembly 102 as illustrated in FIGS. 1 and 5A is secured to the hip screw 4 which directs the surgeon to a second incision and a proximal entry point 104 at the tip of greater trochanter. A drill is placed through the first guide assembly at the second incision and proximal entry point 104 in the direction of the arrow 106 illustrated in FIGS. 1 and 5 to open a hole in the proximal femur. The guide assembly 102 and drill are then removed and the gliding mechanism is inserted into the hip screw 4 as follows.

Where the fixed angle gliding mechanism 6 of the type illustrated in FIGS. 1–4C and described in the related discussion is used, the gliding mechanism 6 is inserted so that throughhole 24 is aligned with the femoral shaft and slots 16 and 18 in the barrel portion 14 of the hip screw 4. Although not illustrated, either of gliding mechanism 6 or the interior wall of barrel portion 14 of the hip screw 4 may be provided with one or more alignment tabs while the other is provided with one or more corresponding channels to ensure that gliding mechanism 6 aligns with slots 16 and 18 upon its insertion into the hip screw 4.

Where the variable angle gliding mechanism 71 of the type illustrated in FIGS. 5A 5B and 6 is used, only the far part comprising the washer 74 and the bushing 78 are inserted into the hip screw 4.

For either gliding mechanism 6 or 71, the intramedullary nail is then inserted through the entry point 104 in the tip of the greater trochanter. For the fixed angle gliding mechanism 6 the intramedullary nail 8 through 8H is threaded through the slot 16, throughhole 24 and slot 18 as the intramedullary nail 8 through 8H is inserted into the femur's intramedullary canal. For the variable angle gliding mechanism 71, the intramedullary nail 8I or 8J is threaded through slot 16, adjacent to and past the inserted portion of the gliding mechanism 71 (e.g., washer 74 and bushing 78) through slot 18 and into the femur's intramedullary canal.

The intramedullary nail is advanced until the recess 44, throughhole 54 or slots 84 and 86 align with the gliding mechanism being used. Alternatively, as illustrated in FIG. 3C the intramedullary nail 8E is advanced until it is in the position desired by the surgeon, which is not limited by the alignment of the intramedullary nail with the gliding mechanism for the embodiment illustrated in FIG. 3C.

For the fixed angle gliding mechanism 6 illustrated in FIGS. 2, 3A, 3B and 3C, the set screw 38, 46 or 56 respectively is then inserted and tightened to secure the gliding mechanism to the intramedullary nail. For the fixed angle gliding mechanism 6 illustrated in FIG. 4, the compression screw 68 is then inserted to secure the gliding mechanism 6 to the intramedullary nail. For the variable angle gliding mechanism 71 illustrated in FIGS. 5A, 5B and 6, the near part (e.g., comprising washer 72 and bushing 76) is then inserted into the barrel portion 14 of the hip screw 4 and the screw 80 is inserted through the bushing 76, washer 72, intramedullary nail 8, washer 74 and bushing 78 and tightened to secure both parts of the two part gliding mechanism 71 about the intramedullary nail 8.

In each of the foregoing, upon securing the intramedullary nail to the selected gliding mechanism as described above, a second guide assembly 108 is then secured to the hip screw 4 which allows for insertion through the femur of locking screws 15 and 17. The guide assembly 108 directs the placement of skin incision and drill holes through the femur through which these screws are placed to coincide with throughholes 11 and 13, respectively. The guide assembly 108 is then removed and the locking screws 15 and 17 are inserted by the surgeon. In an alternative embodiment, the guide assemblies 102 and 108 may be formed as a single unit as opposed to two separate units. Further, in yet another embodiment of the present invention, the locking screws 15 and 17 may be located by the surgeon using other procedures, as for example by locating the throughholes 11 and 13 using an x-ray or other device. In a preferred embodiment of the present invention, where the intramedullary nail is of the type of intramedullary nail 8 or 8B–8J, the surgeon locates the throughholes 11 and 13 using an x-ray device and where an intramedullary nail of the type of intramedullary nail 8A of FIG. 1B is used, the surgeon preferably locates the throughholes 11 and 13 using the guide assembly 102.

With the exception of the embodiment illustrated in FIGS. 4A, 4B, and 4C where a compression screw is already in place, in any of the other embodiments described above, where a compression screw is utilized such as compression screw 10 described above, the surgeon now has the option of inserting the compression screw 10 in the hip screw 4 if static compression of the fracture is desired. Where a compression screw 10 has been placed into the hip screw 4, it is then advanced until the degree of compression desired by the surgeon is achieved.

The surgical sites are closed in the usual fashion. However, as noted above, the surgeon may at any time access the compression screw 10 where present to provide more compressive force during the healing process.

As may be appreciated from the foregoing, the present invention provides a novel orthopedic implant which is surgically minimally invasively implanted, allows custom fitting of the implant to the dimensions of the femur of a patient, allows for static compression to be applied at the time of surgery as well as allowing for dynamic controlled collapse of the fracture during the healing process and which allows fixation to the shaft of the femur by an intramedullary nail. The present invention provides an orthopedic implant which is intramedullary; is capable of providing static plus dynamic compression; and which is of the hip screw implantation-first design, combining attributes and providing functionality which has heretofore been unknown in the art.

It will be readily appreciated by those skilled in the art that modifications may be made to the invention without departing from the concepts disclosed in the foregoing description. Such modifications are to be considered as included within the scope of the appended claims unless the claims, by their language, expressly stated otherwise. Accordingly, the particular embodiments described in detail hereinabove are illustrative only and are not limiting as to the scope of the invention, which is to be given the full breadth of the appended claims and any and all equivalents thereof.

I claim:

1. An orthopedic implant comprising:
   a) a hip screw including a first section which includes a means for securing said hip screw into the head of a femur and a second section, said second section including a barrel portion, said barrel portion having a hollow core extending along the longitudinal axis of the hip screw and including a pair of opposed slots in the barrel portion extending along a portion of the longitudinal axis of the barrel portion;
   b) a gliding mechanism adapted to provide a slidable fit within said hollow core along the longitudinal axis of said hip screw and further including a throughhole therethrough generally transverse of the longitudinal axis of the hip screw, said throughhole adapted to receive an intramedullary nail, said throughhole aligning with said pair of opposed slots;
   c) an intramedullary nail having a longitudinal axis generally transverse of the longitudinal axis of the hip screw, said intramedullary nail extending through said pair of opposed slots in said barrel portion and through said throughhole in said gliding mechanism; and
   d) a means for preventing relative motion of said gliding mechanism with said intramedullary nail after said intramedullary nail has been inserted through said throughhole in said gliding mechanism.

2. The orthopedic implant of claim 1 wherein said intramedullary nail has a cross section of any geometric shape, the shape and dimensions of which cross section may be generally the same along the entire length of said intramedullary nail or may vary along the length of said intramedullary nail.

3. The orthopedic implant of claim 2 wherein said intramedullary nail is twisted along its longitudinal axis.

4. The orthopedic implant of claim 1 wherein said means for preventing relative motion comprises:
   a) a bore through at least a portion of said gliding mechanism, said bore extending generally parallel with the longitudinal axis of the barrel portion and generally transverse of said throughhole, said bore extending from the exterior of said gliding mechanism at least as far as said throughhole, said bore further including threads along at least a portion of said bore; and
   b) a set screw adapted to threadably engage said threads in said bore, whereupon said set screw impinges upon said intramedullary nail as said set screw is advanced along said threads of said bore thereby affixing said intramedullary nail to said gliding mechanism to prevent relative motion of said gliding mechanism with said intramedullary nail.

5. The orthopedic implant of claim 4 wherein said set screw further comprises a first portion having external threads thereon adapted to threadably engage said threaded portion of said bore in said gliding mechanism and a second portion adapted to impinge upon said intramedullary nail and a means for swiveling said first portion of said set screw relative to said second portion of said set screw.

6. The orthopedic implant of claim 1 further comprising a means for urging said gliding mechanism along said barrel portion toward said first section of said hip screw.

7. The orthopedic implant of claim 6 wherein said means for urging comprises:
   a) threads extending along at least a portion of the interior surface of the barrel portion; and
   b) a compression screw adapted to threadably engage said threads extending along said interior surface of said barrel portion, whereupon rotating said compression screw in said threads extending along said interior portion of said interior surface of the said barrel portion causes said compression screw to contact said gliding mechanism and urge said gliding mechanism along said barrel portion toward said first section of said hip screw.

8. The orthopedic implant of claim 7 wherein said means for urging includes said means for preventing relative motion of said gliding mechanism with said intramedullary nail.

9. The orthopedic implant of claim 8 wherein said means for preventing relative motion comprises:
   a) a pin associated with said compression screw, said pin extending parallel with the longitudinal axis of said barrel portion along at least a portion of the barrel portion of the hip screw;
   b) a bore through said gliding mechanism, said bore extending through at least a portion of said gliding mechanism, said bore extending generally parallel with the longitudinal axis of the barrel portion and generally transverse of said throughhole, said bore extending from the exterior of said gliding mechanism at least as far as said throughhole, said bore adapted to receive said pin;
   c) a means for affixing said pin to said intramedullary nail selected from the group consisting of providing a throughhole through said intramedullary nail adapted to receive said pin and impinging said pin on a surface of said intramedullary nail;

said bore in said gliding mechanism and said pin and said throughhole through said intramedullary nail when present adapted to align with one another when said intramedullary nail is inserted through said throughhole in said gliding mechanism; and whereupon advancing said compression screw along said threads on the interior surface of said barrel portion advances said pin through said bore in said gliding mechanism, whereupon said pin passes through said throughhole in said intramedullary nail when present or impinges upon said intramedullary nail when no such throughhole is present, whereupon relative motion of said intramedullary nail and said gliding mechanism is prevented by said pin passing through or impinging upon said intramedullary nail.

10. The orthopedic implant of claim 1 wherein said means for securing said hip screw into the head of a femur includes:
  a) a bore through at least a portion of said head of said femur; and
  b) threads along at least a portion of the exterior surface of said first section of said hip screw, wherein said external treads on the exterior surface of said first section threadably engage the wall of said bore in said head of said femur.

11. The orthopedic implant of claim 1 wherein said means for securing said hip screw into the head of a femur includes:
  a) a bore through at least a portion of the head of said femur; and
  b) a friction fit of said first section in said bore in said head of said femur to secure said hip screw into said head of said femur.

12. The orthopedic implant of claim 1 wherein said gliding mechanism is a one piece gliding mechanism.

13. The orthopedic implant of claim 1 wherein said gliding mechanism is a two piece gliding mechanism.

14. The orthopedic implant of claim 13 wherein said two piece gliding mechanism comprises:
  a) a first compression member;
  b) a second compression member; and
  c) a means for urging said first compression member and said second compression member toward one another about said intramedullary nail to provide said throughhole in said gliding mechanism adapted to receive said intramedullary nail.

15. The orthopedic implant of claim 14 further comprising a means for urging said two piece gliding mechanism along said barrel portion toward said first section of said hip screw.

16. The orthopedic implant of claim 15 wherein said means for urging comprises:
  a) threads extending along at least a portion of the interior surface of the barrel portion; and
  b) a compression screw adapted to threadably engage said threads extending along said interior surface of said barrel portion, whereupon rotating said compression screw in said threads extending along said interior portion of said interior surface of the said barrel portion causes said compression screw to contact said gliding mechanism and urge said gliding mechanism along said barrel portion toward said first section of said hip screw.

17. The orthopedic implant of claim 14 wherein said means for preventing relative motion of said gliding mechanism with said intramedullary nail after said intramedullary nail has been inserted through said throughhole in said gliding mechanism is provided by said means for urging said first compression member and said second compression member toward one another.

18. The orthopedic implant of claim 17 wherein said means for urging said first compression member and said second compression member toward one another comprises:
  a) a throughhole through said first compression member, said throughhole extending generally parallel with the longitudinal axis of the barrel portion of the hip screw;
  b) a throughhole through said second compression member, said throughhole extending generally parallel with the longitudinal axis of the barrel portion of the hip screw, said throughhole through said second compression member further comprising threads along at least a portion of said throughhole;
  c) a throughhole through said intramedullary nail, said throughhole through said intramedullary nail, said throughhole through said first compression member and said throughhole through said second compression member adapted to generally align with one another when said intramedullary nail has been inserted through said gliding mechanism; and
  d) a connecting screw having a head extending through said throughhole in said first compression member, through said throughhole in said intramedullary nail and through said throughhole in said second compression member, said connecting screw adapted to threadably engage with the threads in said second compression member, whereupon advancing said connecting screw along said threads in said second compression member urges said first and second compression members toward one another between said head of said connecting screw and said threads in said second compression member and whereupon relative motion of the two piece gliding mechanism with the intramedullary nail is prevented.

19. The orthopedic implant of claim 18 wherein said throughhole in said intramedullary nail is in the form of a pair of opposed slots extending along a portion of the intramedullary nail along the longitudinal axis of the intramedullary nail.

20. The orthopedic implant of claim 19 wherein said intramedullary nail has an external surface, a portion of said surface including a plurality of notches, said portion including said notches in contact with a surface of said first compression member and in contact with a surface of said second compression member, wherein the surfaces of the first compression member and the second compression respectively include a plurality of notches adapted to interlock with said notches on said surface of said intramedullary nail, whereupon advancing said connecting screw along said threads in said second compression member urges said first compression member and said second compression member into said notches thereby retaining said connecting screw at an angle relative to the longitudinal axis of the intramedullary nail that said connecting screw has been inserted through said pair of opposed slots in said intramedullary nail, thereby retaining the first and second compression members in relative positions along the external surface of the intramedullary nail.

21. The orthopedic implant of claim 20 wherein the angle is selected from the group consisting of a right angle, an acute angle and an obtuse angle.

22. The orthopedic implant as claimed in claim 14 wherein said first compression member includes a washer and bushing and the second compression member includes a washer and bushing.

23. The orthopedic implant as claimed in claim 22 wherein the bushing of the second compression member includes said threads which threadably engage said connecting screw.

24. The orthopedic implant as claimed in claim 23 wherein the intramedullary nail is inserted through the slots of the hip screw, the connecting screw is disposed within a central bore of the first bushing, the first washer, the second washer, and the second bushing, respectively, and the connecting screw is threadably engaged with the threads of the central bore of the second bushing such that the first bushing, the first washer, the second washer, and the second bushing are securely clamped about the intramedullary nail.

25. A method of inserting an orthopedic implant for the treatment of intertrochanteric fractures comprising the steps of:
   a) affixing a hip screw into the head of a femur, said hip screw including a first section which includes a means for securing said hip screw into the head of a femur and a second section, said second section including a barrel portion, said barrel portion having a hollow core extending along the longitudinal axis of the hip screw and including a pair of opposed slots in the barrel portion extending along a portion of the longitudinal axis of the barrel portion;
   b) inserting a gliding mechanism into said barrel portion of said hip screw, said gliding mechanism adapted to provide a slidable fit within said hollow core along the longitudinal axis of said hip screw and further including a throughhole therethrough generally transverse of the longitudinal axis of the hip screw, said throughhole adapted to receive an intramedullary nail, said throughhole aligning with said pair of opposed slots;
   c) inserting an intramedullary nail through said gliding mechanism, said intramedullary nail having a longitudinal axis generally transverse of the longitudinal axis of the hip screw, whereupon during said intramedullary insertion step said intramedullary nail is inserted through said first opposed slots in said barrel portion through said throughhole in said gliding mechanism and through said second opposed slot and is positioned where deemed surgically necessary by the operating physician; and
   d) associating said gliding mechanism with said intramedullary nail in a manner that prevents relative motion of said gliding mechanism with said intramedullary nail after said intramedullary nail has been inserted through said throughhole in said gliding mechanism.

26. The method of claim 25 further comprising applying an intraoperative compressive force comprising the step of urging said gliding mechanism along said barrel portion toward said first section of said hip screw.

27. The method of claim 26 wherein said urging step comprises:
   a) providing threads extending along at least a portion of the interior surface of the barrel portion; and
   b) providing a compression screw adapted to threadably engage said threads extending along said interior surface of said barrel portion; and
   c) rotating said compression screw in said threads extending along said interior portion of said interior surface of the said barrel portion, whereupon said rotating causes said compression screw to contact said gliding mechanism and urge said gliding mechanism along said barrel portion toward said first section of said hip screw.

28. The method of claim 27 wherein said step of urging includes said step of preventing relative motion of said gliding mechanism with said intramedullary nail.

29. The method of claim 28 wherein said steps of urging and preventing relative motion comprise the steps of:
   a) associating a pin with said compression screw, said pin extending parallel with the longitudinal axis of said barrel portion along at least a portion of the barrel portion of the hip screw;
   b) providing a bore through said gliding mechanism, said bore extending through at least a portion of said gliding mechanism, said bore extending generally parallel with the longitudinal axis of the barrel portion and generally transverse of said throughhole, said bore extending from the exterior of said gliding mechanism at least as far as said throughhole, said bore adapted to receive said pin;
   c) providing a means for affixing said pin to said intramedullary nail selected from the group consisting of providing a throughhole through said intramedullary nail adapted to receive said pin and impinging said pin on a surface of said intramedullary nail;
   d) aligning said bore in said gliding mechanism and said pin and said throughhole through said intramedullary nail when present; and
   whereupon advancing said compression screw along said threads on the interior surface of said barrel portion advances said pin through said bore in said gliding mechanism, whereupon said pin passes through said throughhole in said intramedullary nail when present or impinges upon said intramedullary nail when no such throughhole is present in said intramedullary nail, whereupon relative motion of said intramedullary nail and said gliding mechanism is prevented by said pin passing through or impinging upon said intramedullary nail.

30. The orthopedic implant of claim 4 wherein said intramedullary nail has a cross section of any geometric shape, the shape and dimensions of which cross section may be generally the same along the entire length of said intramedullary nail or may vary along the length of said intramedullary nail.

31. The orthopedic implant of claim 30 wherein said intramedullary nail is twisted along its longitudinal axis.

32. The orthopedic implant of claim 9 wherein said intramedullary nail has a cross section of any geometric shape, the shape and dimensions of which cross section may be generally the same along the entire length of said intramedullary nail or may vary along the length of said intramedullary nail.

33. The orthopedic implant of claim 32 wherein said intramedullary nail is twisted along its longitudinal axis.

34. The orthopedic implant of claim 12 wherein said intramedullary nail has a cross section of any geometric shape, the shape and dimensions of which cross section may be generally the same along the entire length of said intramedullary nail or may vary along the length of said intramedullary nail.

35. The orthopedic implant of claim 34 wherein said intramedullary nail is twisted along its longitudinal axis.

36. The orthopedic implant of claim 13 wherein said intramedullary nail has a cross section of any geometric shape, the shape and dimensions of which cross section may be generally the same along the entire length of said intramedullary nail or may vary along the length of said intramedullary nail.

37. The orthopedic implant of claim 36 wherein said intramedullary nail is twisted along its longitudinal axis.

38. The method of claim 25 wherein the intramedullary nail that is inserted through the throughhole of the gliding mechanism and the opposed slots of the barrel portion of the hip screw has a cross section of any geometric shape, the shape and dimensions of which cross section may be generally the same along the entire length of said intramedullary nail or may vary along the length of said intramedullary nail.

39. The method of claim 38 wherein said intramedullary nail is twisted along its longitudinal axis.

* * * * *